United States Patent [19]

Makino et al.

[11] Patent Number: 5,097,135
[45] Date of Patent: Mar. 17, 1992

[54] METHOD OF FORMING A TWO-DIMENSIONAL DISTRIBUTION IMAGE OF ION CONCENTRATION IN A CELL

[75] Inventors: Tohru Makino; Kazuho Ozaki, both of Hachioji; Atsuo Miyakawa, Fuchu, all of Japan

[73] Assignee: Olympus Optical Co., Ltd., Tokyo, Japan

[21] Appl. No.: 563,251

[22] Filed: Aug. 6, 1990

[30] Foreign Application Priority Data

Aug. 24, 1989 [JP] Japan .................. 1-218366

[51] Int. Cl.⁵ .............................. G01N 21/64
[52] U.S. Cl. ................ 250/461.1; 250/459.1; 250/461.2; 436/172
[58] Field of Search ............ 436/172, 63; 364/485; 250/459.1, 461.1, 461.2

[56] References Cited

U.S. PATENT DOCUMENTS

| | | | |
|---|---|---|---|
| 4,006,360 | 2/1977 | Mueller | 250/461.2 |
| 4,492,752 | 1/1985 | Hoffman et al. | 250/461.2 |
| 4,495,293 | 1/1985 | Shaffer | 436/172 |
| 4,604,520 | 8/1986 | Pohl | 250/216 |
| 4,631,750 | 12/1986 | Gabriel et al. | 382/41 |
| 4,668,868 | 5/1987 | Noller | 250/458.1 |

OTHER PUBLICATIONS

Nature, vol. 318, Dec. 12, 1985, pp. 558-561, Williams et al., "Calcium Gradients in Single Smooth Muscle Cells Revealed by Digital Imaging Microscope Using Fura-2".

Primary Examiner—Constantine Hannaher
Assistant Examiner—Jacob M. Eisenberg
Attorney, Agent, or Firm—Frishauf, Holtz, Goodman & Woodward

[57] ABSTRACT

This invention relates to a method of forming a two-dimensional concentration distribution image of specific ions to be assayed in a living cell, on the basis of the variation in fluorescent spectrum or excitation spectrum of a fluorescent probe. This method comprises the steps of administering a fluorescent probe into a cell, obtaining a fluorescence intensity distribution image by determining fluorescence light from the fluorescent probe in a region including the cell, measuring the cell optically, thereby obtaining a cell image of the cell selected from the group consisting of a bright-field image, a phase contrast image, a Nomarski differential interference contrast image, and a polarization image, determining a background fluorescence value from a profile of the fluorescence intensity image and a profile of the cell image, forming a two-dimensional concentration distribution image of the ions to be assayed, by image processing including a subtraction of the background fluorescence value from the fluorescence intensity distribution image, and subjecting the cell image and the two-dimensional concentration distribution image of the ions to image processing, thereby displaying both images in an overlapping manner.

6 Claims, 8 Drawing Sheets

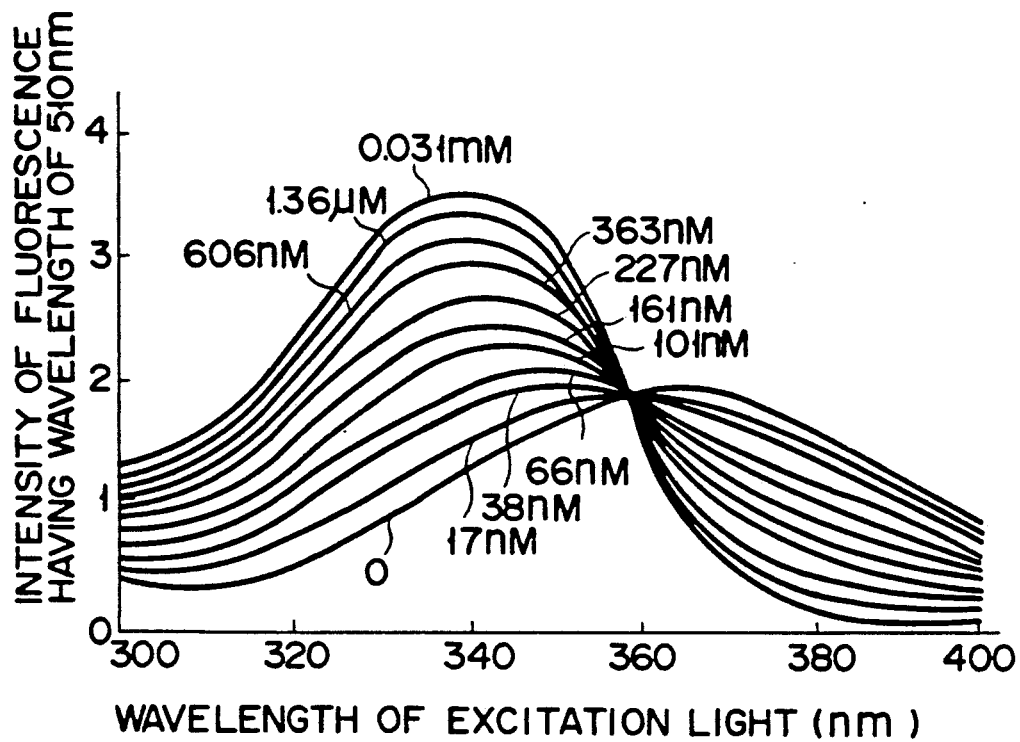
F I G. 1
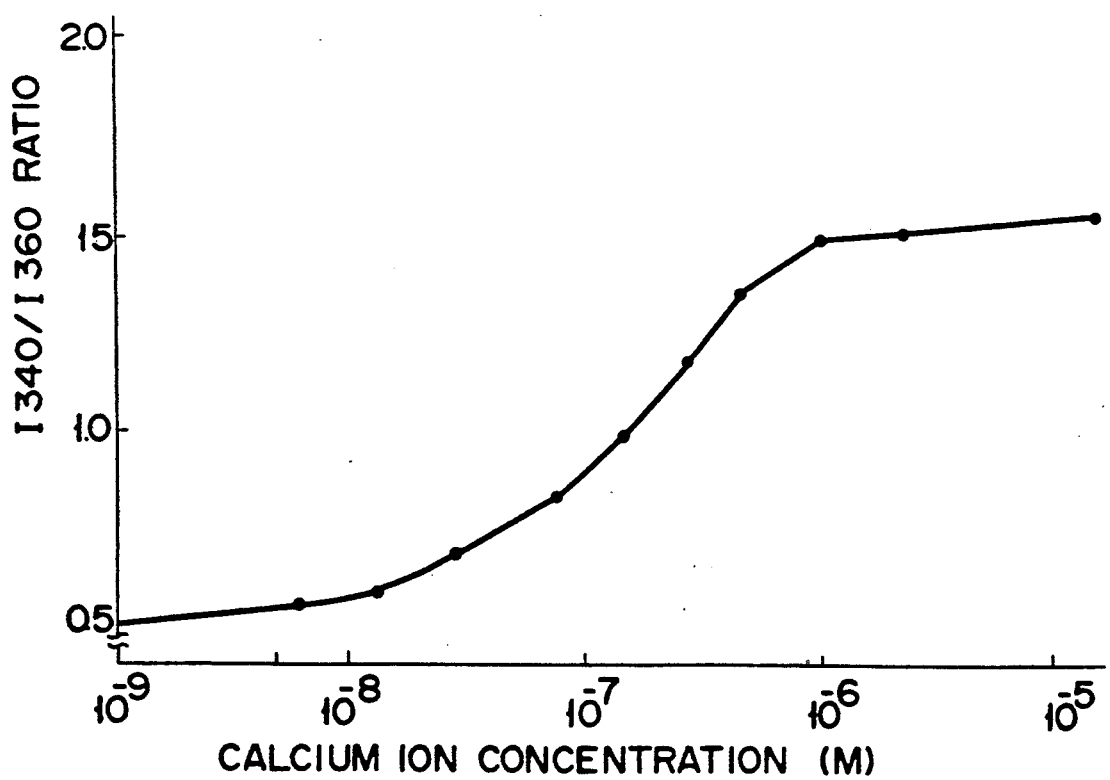
F I G. 2

F I G. 9
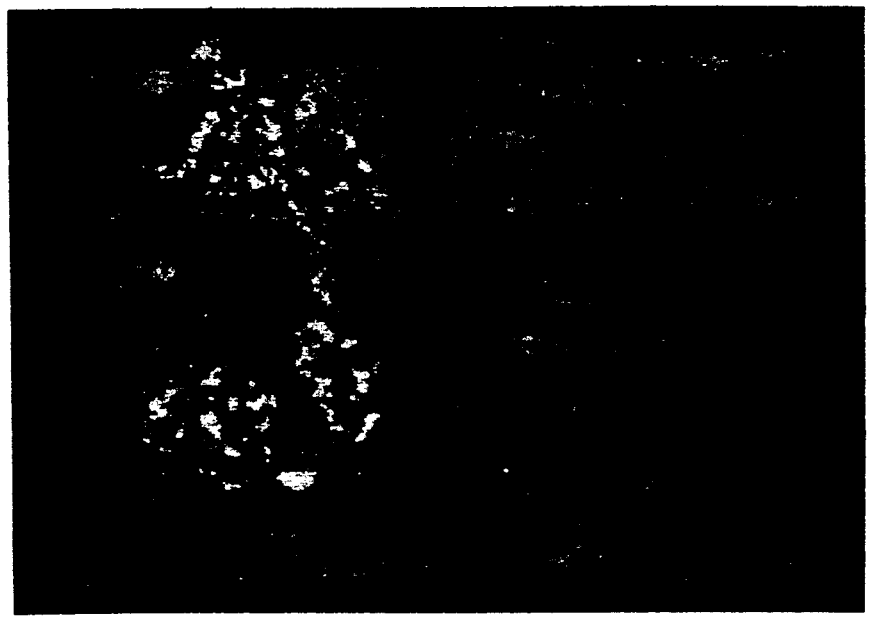
F I G. 11

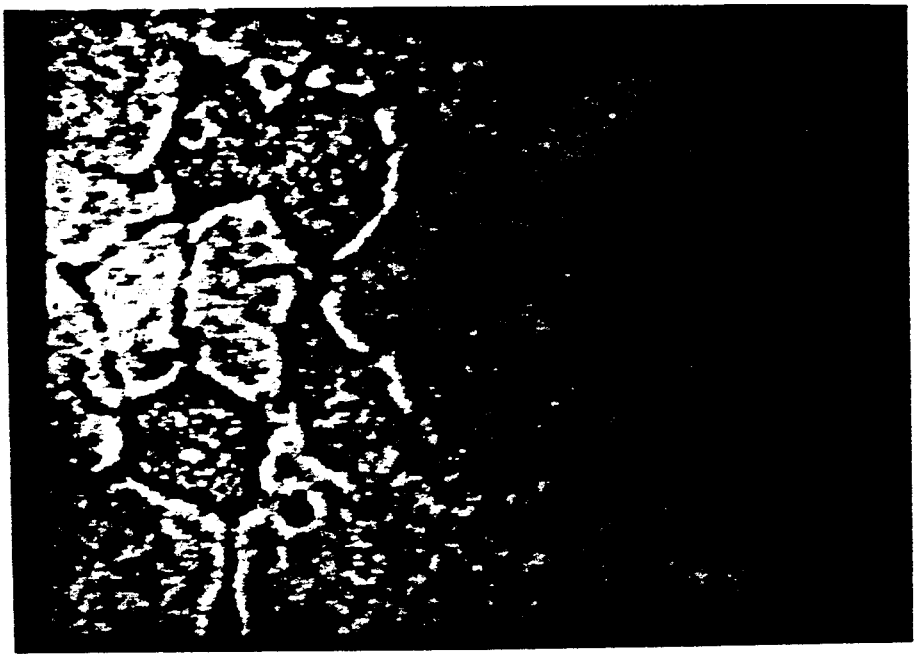
F I G. 12

METHOD OF FORMING A TWO-DIMENSIONAL DISTRIBUTION IMAGE OF ION CONCENTRATION IN A CELL

BACKGROUND OF THE INVENTION

1. Field of the Invention

The present invention relates generally to a method of forming a two-dimensional distribution image of calcium ion concentration, hydrogen ion concentration, etc. in a cell, by use of a fluorescent microscope system in which a fluorescent reagent is employed as a probe. More particularly, this invention relates to a method of clearly displaying an image of a cell contour, and displaying the two-dimensional distribution image of the ion concentration in precise positional relationship with the cell contour.

2. Description of the Related Art

Recently, in the fields of neuroscience and cell biology, a method of determining the concentration of free calcium ions in a living cell has widely been employed to study the metabolic function of a cell. In this method, a suitable fluorescent reagent (hereinafter, referred to as "fluorescent probe") capable of functioning as a probe for assaying a target substance is introduced into a living cell. On the basis of the fluorescence intensity of the probe, the concentration of a target chemical species is determined. This method is carried out to assay various kinds of ions in a cell, such as calcium ions, sodium ions, magnesium ions, and chlorine ions, or macromolecules in a cell, such as protein or nucleic acid. The principle of assaying will now be explained.

When the fluorescent probe is bonded to a specific substance to be assayed, its fluorescence spectrum or excitation spectrum is changed. The degree of change differs in accordance with the concentration of the substance. Thus, if the fluorescence intensity of the probe is measured by means of a fluorescent spectrophotometer or a fluorescent microscope, the concentration of the specific substance can be determined on the basis of the change in the spectrum. For example, when calcium ions in a cell are determined, fura-2 is administered as a fluorescent probe, and the change in excitation spectrum caused by the specific bonding between the probe and calcium ions is measured. When a fluorescent microscope is used, it is noted that the change in fluorescence intensity is measured with respect to not the entire fluorescent image but a specific small circular region of the fluorescent image.

According to the above method, the concentration of calcium ions in a specific small region of a cell can easily been determined, but it is very difficult to find a concentration distribution of calcium ions in a relatively large two-dimensional region. In order to obtain such a concentration distribution, it is necessary to measure samples taken at many points, and a great deal of time and work is required. On the other hand, in the fields of neuroscience and cell biology, it is very important to find a distribution of calcium ion concentration in a relatively large region including, e.g. several cells. Under the situation, there is a demand for an improved method of easily obtaining a two-dimensional concentration distribution by measuring, at a time, the concentration of a target substance to be assayed in a relatively large two-dimensional region.

To meet such a demand, U.S. Pat. application Ser. No. 340,236, filed on Apr. 19, 1989 proposes a fluorescent microscope system combined with an image processing technique. The disclosure in said U.S. Pat. application which falls within the scope of this invention is incorporated in the present specification. The use of this fluorescent microscope system makes it possible to easily obtain an intracellular ion concentration distribution in a relatively large two-dimensional region. This type of fluorescent microscope is employed in a preferred embodiment of the present invention. Thus, the microscope will be described in detail in the description of the embodiment of the present invention.

Even if the above-stated fluorescent microscope system is employed, however, the following problems occur in the conventional method of obtaining a two-dimensional distribution of the intracellular ion concentration.

When the physiological function of a cell is studied, it is very important to obtain data as to in which portion of the cell the concentration of free calcium ions increases or decreases. However, a fluorescence intensity image obtained by the conventional method generally includes only data relating to an ion concentration, and does not include data relating to the positional relationship between the ion concentration and the cell. Thus, even if the obtained fluorescence intensity image is image-processed, it is not possible to obtain an image wherein the ion concentration distribution is related to the contour of the cell.

In addition, the obtained fluorescence intensity image includes background fluorescence outside the cell. In order to find a two-dimensional concentration distribution of ions to be assayed, the background fluorescence must be subtracted from the fluorescence intensity image. It is difficult, however, to determine the value of background fluorescence objectively. According to the conventional method, an experimenter determines the value of a background level empirically on the basis of a profile of a fluorescence intensity image. Thus, the basis for determining the value of a background level is uncertain, and varies from experimenter to experimenter. It is therefore difficult to precisely determine the ion concentration.

SUMMARY OF THE INVENTION

An object of the present invention is to obtain a two-dimensional concentration distribution image of specific ions in a cell in relation to the contour of the cell, by use of a fluorescent microscope system using a fluorescent probe.

Another object of the invention is to provide a method of objectively determining the level of background fluorescence light and exactly measuring the ion concentration.

These objects are achieved by a method of forming a two-dimensional concentration distribution image of specific ions to be assayed in a living cell, on the basis of the variation in fluorescent spectrum or excitation spectrum of a fluorescent probe, said method comprising the steps of:

administering a fluorescent probe into a cell;

obtaining a fluorescence intensity distribution image by determining fluorescence light from the fluorescent probe in a region including the cell;

measuring the cell optically, thereby obtaining a cell image of the cell selected from the group consisting of a bright-field image, a phase contrast image, a Nomarski differential interference contrast image, and a polarization image;

determining a background fluorescence value from a profile of the fluorescence intensity image and a profile of the cell image;

forming a two-dimensional concentration distribution image of the ions to be assayed, by image processing including a subtraction of the background fluorescence value from the fluorescence intensity distribution image; and subjecting the cell image and the two-dimensional concentration distribution image of the ions to image processing, thereby displaying both images in an overlapping manner.

According to the method of this invention, in order to determine the background fluorescence value, not only is a profile of a fluorescence intensity image used, but also a profile of a cell image, which is selected from the group consisting of a bright-field image, a phase contrast image, a Nomarski differential interference contrast image and a polarization image, is used as a reference image. Thus, an experimenter's subjective judgment can be avoided, and the background fluorescence value can be determined exactly and objectively. Therefore, the ion concentration and concentration distribution can be found exactly.

In addition, since the two-dimensional concentration image of ions to be assayed is overlapped with the cell image, the relationship between the concentration distribution and the cell structure is made clear. Therefore, it is clearly understood which part of a cell corresponds to the ion concentration at each point of the concentration distribution image.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate a presently preferred embodiment of the invention, and together with the general description given above and the detailed description of the preferred embodiment given below, serve to explain the principles of the invention.

FIGS. 1 to 4 are graphs for explaining the principles of an ion concentration determining method using a fluorescent probe;

FIG. 9 is a photograph showing a bright-field image of cells, according to the embodiment of the invention;

FIG. 11 is a photograph showing a two-dimensional distribution image of calcium ions, which was obtained in the embodiment of the invention; and FIG. 12 is a photograph showing an overlapped image of a bright field image and a two-dimensional distribution image of calcium ions, which was obtained in the embodiment of the invention.

DETAILED DESCRIPTION OF THE PREFERRED EMBODIMENTS

Figure 3:
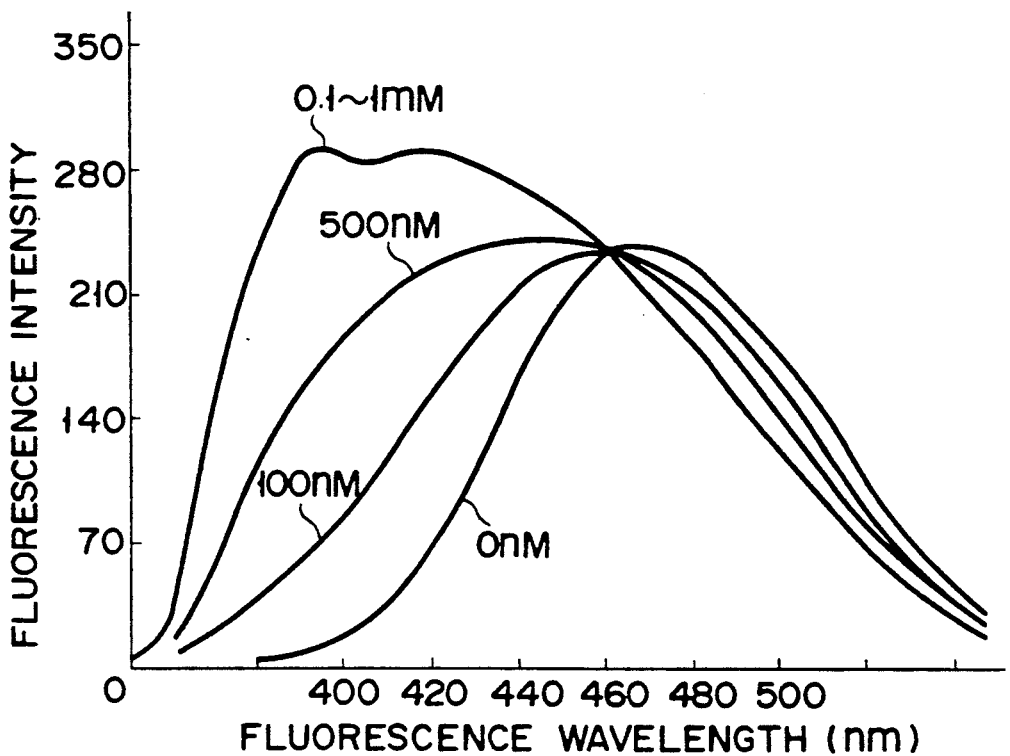

In order to better the understanding of the present invention, a method of determining the concentration of a target substance in a living cell, by use of a fluorescent probe, will now be described in greater detail.

As has been described above, this method employs a fluorescent probe having an excitation spectrum or a fluorescence spectrum being variable in accordance with the concentration of specific ions. For example, when the concentration of calcium ions is determined, fluorescent reagents commercially available under the tradenames of fura-2, Quin-2 and Indo-1 (manufactured by Molecular Probes, Inc.) may be used as the fluorescent probe.

The fluorescent reagent, fura-2, is expressed by structural formula (I) shown below. The reagent having a free carboxyl group is unable to pass through a cell membrane of an established nerve cell line (NG108, N115) or an established cell line derived from glia cell (C6Bu-1). Thus, fura-2 is administered to a sample cell in the form of fura-2/AM which is an acetoxymethyl esterified derivative and is able to pass through the cell membrane. Once the fura-2/AM is introduced into the cell, it is immediately metabolized and converted to fura-2 which is specifically bonded to calcium ions.

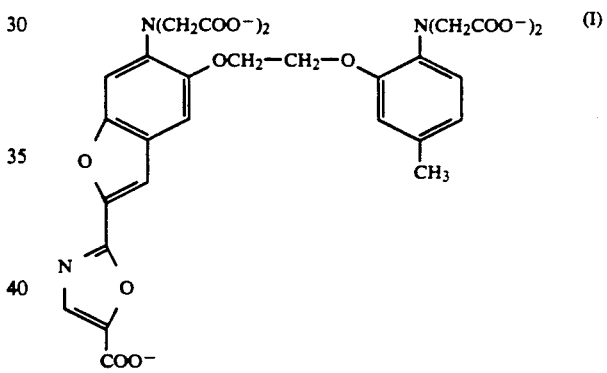

When fura-2 is bonded to calcium ions, the excitation spectrum of fura-2 varies in accordance with the calcium concentration. The fluorescence of fura-2 has a peak at 510 nm and a band pass at 10 nm. FIG. 1 shows spectra which were obtained when the intensity of fluorescence having a wavelength of 510 nm was determined by means of a fluorescent spectrophotometer, while changing the wavelength of excitation light, in the presence of calcium ions of various concentrations. As can be seen from FIG. 1, the variation of fluorescence intensity dependent upon the calcium concentration is greatest when the wavelength of excitation light is 340 nm. By contrast, when the wavelength of excitation light is 360 nm, the variation of the fluorescence intensity dependent upon the calcium concentration is not observed. In addition, when the wavelength of excitation light is 380 nm, the fluorescence intensity varies in a manner reverse to that observed when the wavelength of excitation light is 340 nm.

When the variation of fluorescence intensity dependent upon the calcium concentration is made different by the wavelength of excitation light, a two-wavelength determination method is effective. Specifically, the fluorescent probe is excited at two different wavelengths, and the calcium concentration is determined from the ratio of the fluorescence intensities corresponding to the two excitation wavelengths. One of the two excitation wavelengths is set to a value at which the fluorescence intensity varies to the greatest degree, and the other is set to a value at which the fluorescence intensity does not vary or varies reversely. By using the two-wavelength determination method, the concentration and attenuation of the fluorescent probe and the variation in intensity of excitation light can be normalized. Referring to FIG. 1, the two-wavelength determination method using excitation wavelengths of 340 nm and 360 nm (340 nm for measuring light; 360 nm for reference light) will now be described in greater detail.

Suppose that the fluorescence intensity is I340 when the excitation wavelength is 340 nm, and the fluorescence intensity is I360 when the excitation wavelength is 360 nm. The value of I340/I360 is calculated on the basis of data shown in FIG. 1. The value varies in a range of 0.64 to 1.89, depending upon the calcium concentration.

When a TV camera is employed in determination, it is necessary to take the dynamic range of the TV camera into consideration in order to carry out precise two-wavelength determination. More specifically, since desirable input/output linearity is obtained only in a predetermined dynamic range, it is necessary that the value of I340/I360 (the input to the camera) vary within a dynamic range, in order to obtain a precise output. For this purpose, the intensity of excitation light is controlled by means of a neutral density filter (hereinafter, called "ND filter") and the value of I340/I360 is normalized so that the center value of I340/I360 may become 1. FIG. 2 shows the relationship between the normalized value of I340/I360 and the calcium concentration. The data shown in FIG. 2 can be used as an calibration curve when the calcium concentration is determined by means of a fluorescent microscope system.

Another fluorescent probe used in determining the calcium concentration is Indo-1 that is expressed by structural formula (II) shown below. The reagent having a free carboxyl group is unable to pass through a cell membrane of a living cell. Thus, Indo-1 is administered to a sample cell in the form of Indo-1/AM which is an acetoxymethyl esterified derivative. It is not Indo-1/AM but Indo-1, produced by metabolism in the cell, that is specifically bonded to calcium ions.

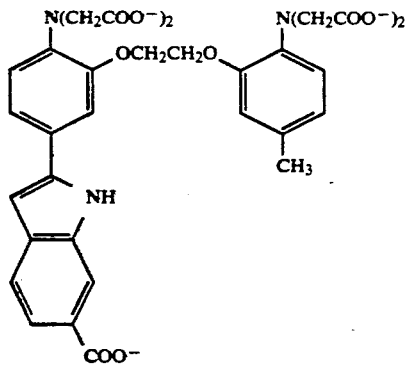
(II)

Figure 4:
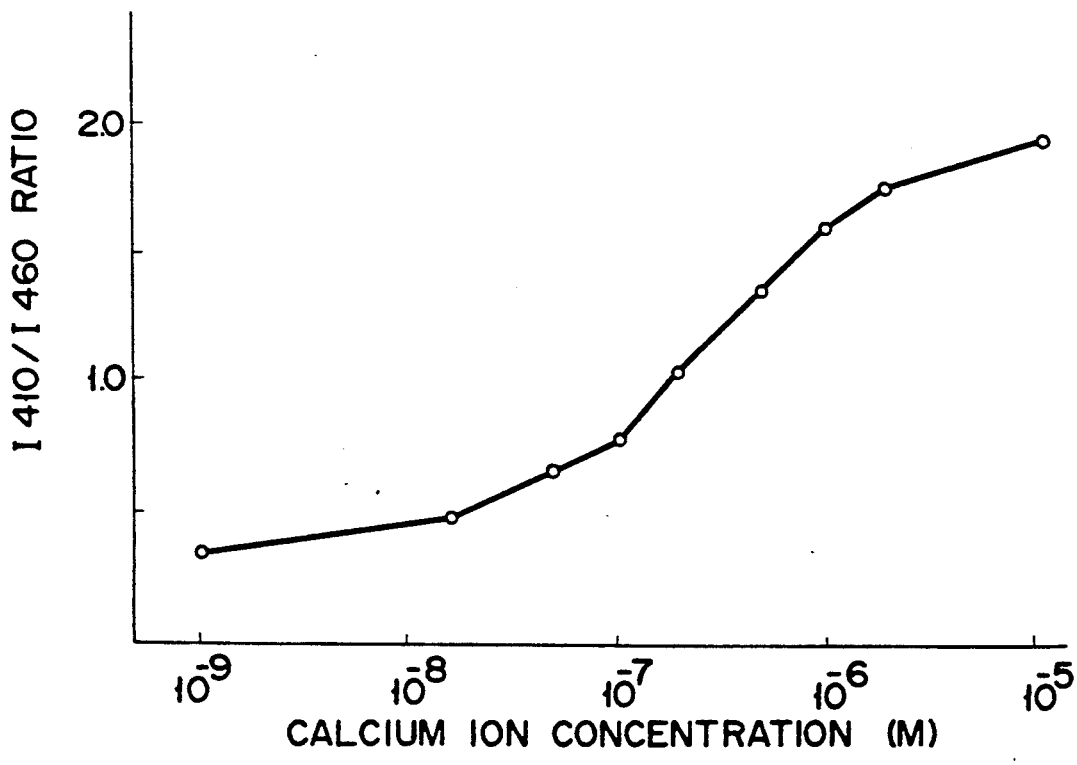

Unlike the case of using fura-2, when Indo-1 is used, the fluorescence spectrum, not the excitation spectrum, varies in accordance with the calcium concentration. FIG. 3 shows spectra which were obtained when excitation light having a wavelength of 340 nm is radiated onto Indo-1 in the presence of calcium ions of various concentrations. As can be seen from the spectra, the variation of fluorescence intensity dependent upon the calcium concentration is greatest when the wavelength of fluorescence is 410 nm or thereabouts. By contrast, when the wavelength of fluorescence is 460 nm, the variation of the fluorescence intensity dependent upon the calcium concentration is not observed. In addition, when the wavelength of fluorescence is in a range of 460 nm to 480 nm, the fluorescence intensity varies in a manner reverse to that observed when the wavelength of fluorescence is 410 nm. while fixing the wavelength of excitation light, the fluorescence intensity is determined at two chosen wavelengths, thereby carrying out a two-wavelength determination method, as in the case of fura-2. Normally, wavelengths of 410 nm and 460 nm, or wavelengths of 410 nm and 480 nm are combined. When a TV camera is employed in determination, the value of I410/I460 or the value of I410/I480 is normalized for the same reason stated above in connection with the case of fura-2. Specifically, the ND filter is used to set the center value of I410/I480 or I410/I480 to 1. FIG. 4 shows the relationship between the normalized value of I410/I460 and the calcium concentration. The data shown in FIG. 4 can be used as an calibulation curve when the calcium concentration is determined by means of a fluorescent microscope system.

The feature of the present invention will now be described.

In the present invention, the background fluorescence value is determined by displaying, desirably on a CRT or the like, a profile obtained along a given line of a fluorescence intensity distribution image and a profile obtained along the given line of a cell image produced as a bright-field image or the like.

As has already been described above, the fluorescence intensity distribution image and the two-dimensional ion concentration distribution image are obtained by a method similar to the method of U.S. Pat. application No. 340,236.

Figure 5:
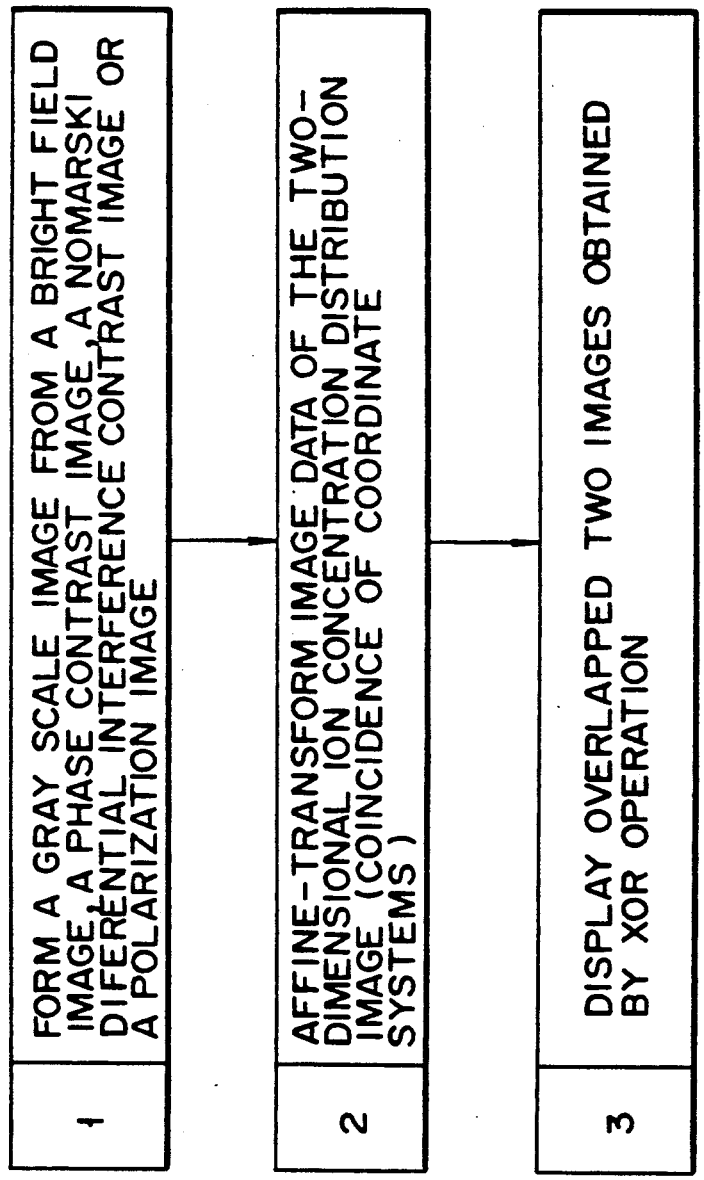
FIG. 5 is a flowchart for illustrating a method of overlapping images in the present invention.

In the present invention, the two-dimensional concentration distribution image of ions to be assayed and the cell image may be overlapped, for example, by the method illustrated in a flowchart of FIG. 5.

In step 1, a cell image formed as a bright-field image, a phase contrast image, a Nomarski differential interference contrast image, or a polarization image by optically determining a cell is converted to a gray scale image on the basis of the luminance of the cell image. The obtained gray scale image is displayed on a CRT display. The two-dimensional concentration distribution image (fluorescent image) of target ion is overlapped on the gray scale image.

In general, the bright-field image, phase contrast image, a Nomarski differential interference contrast image, or polarization image is not exactly overlapped with the fluorescent image. In order to make the coordinates of both images coincide, the image data of the two-dimensional ion concentration distribution image is subjected to affine transformation in step 2. Suppose that the coordinates of an input image are (I, J) and those of an output image are (x, y). Then, the coordinates (x, y) are affine-transformed to (u, v) which are real-number type image coordinates in (I, J). Subsequently, the coordinates (u, v) are interpolated and the interpolated concentration level I' is stored at (x, y). A formula for affine transformation of coordinates is given by:

$$u = a_1 x + a_2 y + a_3$$

$$v = b_1 x + b_2 y + b_3$$

where $a_1$, $a_2$, $a_3$, $b_1$, $b_2$, and $b_3$ are arbitrary coefficients.

The resultant transformed image data of the two-dimensional ion concentration distribution image is colored in accordance with ion concentrations, and is overlapped on the gray scale cell image obtained in step 1. In this case, in order to maintain the data of the gray scale image obtained in step 1, an exclusive-OR operation is carried out at respective locations of coordinates when both images are overlapped (step 3). Thus, the gray scale cell image obtained in step 1 is overlapped with the ion concentration distribution image, and the overlapped image is displayed.

The basic exclusive-OR (XOR) operation is shown below:

| Input A | Input B | Output |
|---------|---------|--------|
| 0 | 0 | 0 |
| 1 | 0 | 1 |
| 0 | 1 | 1 |
| 1 | 1 | 0 |

In accordance with this operation, the gray scale cell image is overlapped with the ion concentration distribution image to produce a composite image in the following manner:

| Cell Image: | ○ | ○ | ○ | x | x | ○ | x | ○ |
|---|---|---|---|---|---|---|---|---|
| Concentration Distribution Image: | x | x | ○ | ○ | x | ○ | x | x |
| Composite Image: | ○ | ○ | x | ○ | x | x | x | ○ |

("○" indicates the state in which data is set on the screen, and "x" indicates the state in which data is not set on the screen.)

The present invention will now be described in greater detail.

Figure 6:
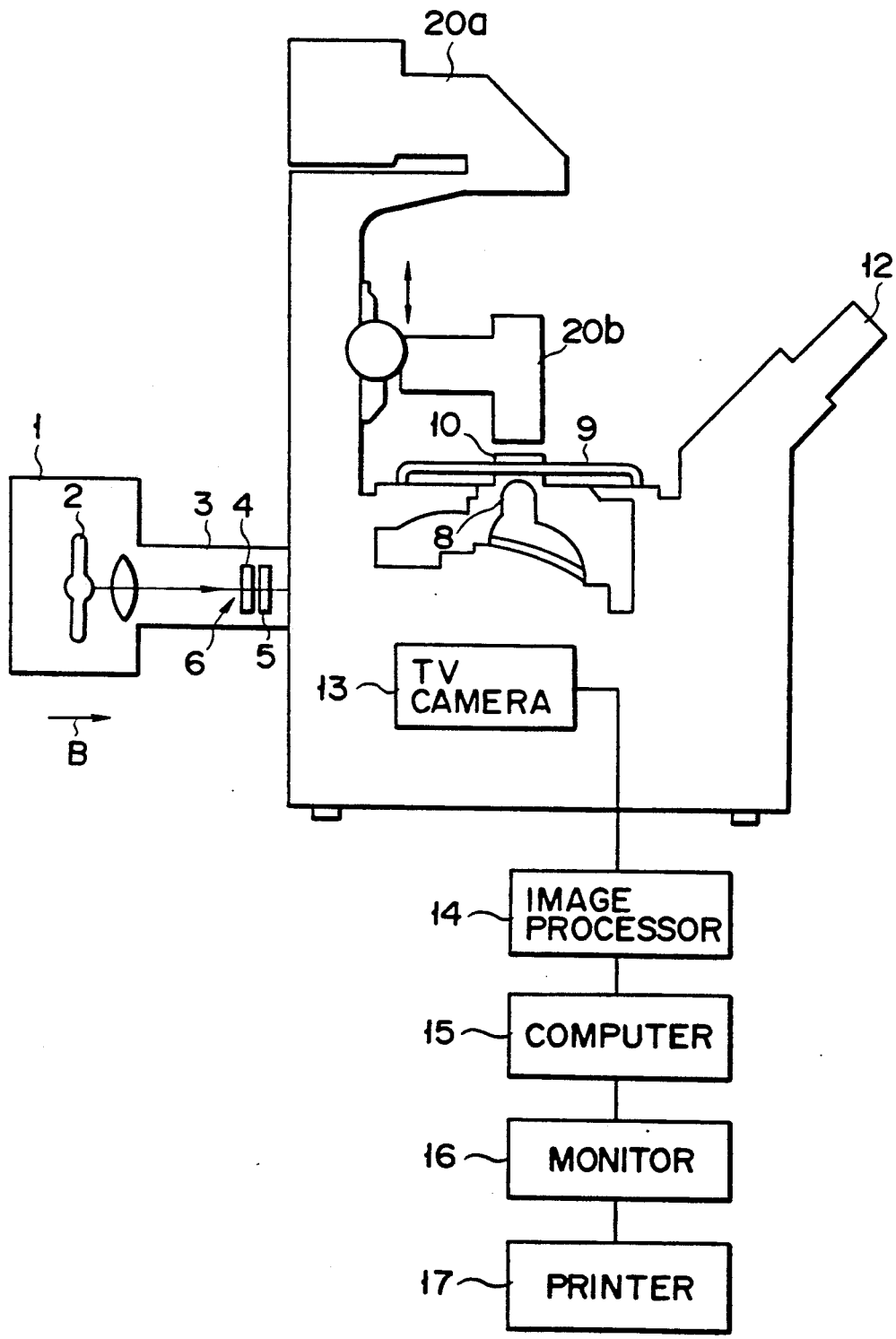
FIG. 6 and FIG. 7 are view for describing a fluorescent microscope system employed in this invention.
Figure 7:
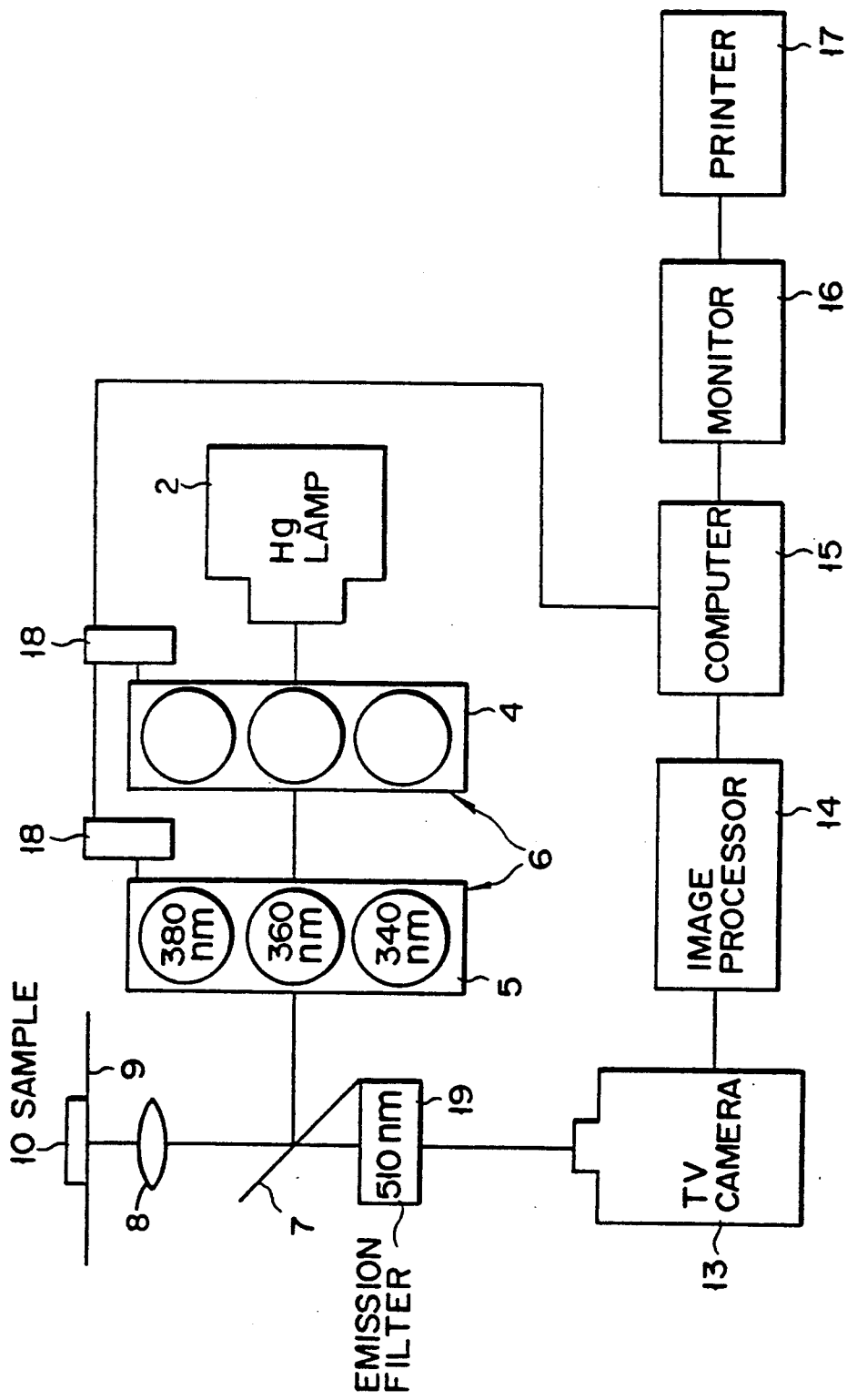

Referring to FIGS. 6 and 7, an example of a fluorescent microscope system suitable for the present invention will be described. FIG. 6 is a schematic view of the fluorescent microscope system, and FIG. 7 is a block diagram showing the same. This system is disclosed in U.S. Pat. application No. 340,236. In this system, a fluorescent microscope of inverted epi-fluorescent type (manufactured by Olympus Optical Co., Ltd., IMT-2) is combined with a TV camera and an image processing apparatus. By virtue of this structure, the fluorescence analysis is carried out, at a time, in a predetermined two-dimensional region, and a calcium concentration distribution can easily be determined. This fluorescent microscope system is designed to perform an analysis on the basis of the variation in excitation spectrum, such as an assay of calcium ions using fura-2 as a fluorescent probe.

In FIG. 6, an illumination apparatus 1 generates excitation light. The illumination apparatus 1 contains a Hg lamp 2 as a light source. The Hg lamp 2 may be replaced with a Xe lamp or any other lamp capable of radiating light of desired wavelength. The illumination apparatus 1 is provided with a projection tube 3 which is coupled to a microscope body. A filter unit 6 comprising a neutral density filter (ND filter) 4 and an interference filter 5 is disposed in the projection tube 3 on an optical axis of the Hg lamp 2. The interference filter 5 allows only light having a predetermined wavelength to pass through. The ND filter 4 controls the amount of passing light at each wavelength. The ND filter 4 may be omitted, if conditions allow.

The excitation light, which has passed through the filter unit 6, enters an objective lens 8 through an optical system (not shown) disposed within the microscope body. The light output from the lens 8 is focused at a sample cell 10 placed on a stage 9. In advance, fura-2 is administered to the sample cell 10, and the sample cell 10 emits fluorescence light by radiation of the excitation light. The emitted epi-fluorescent light is observed through an eyepiece 12 through an optical system (not shown) and is simultaneously supplied to a TV camera 13 (SIT). The TV camera 13 is connected to an image processor 14, a computer 15, a monitor 16 and a printer 17.

The fluorescent microscope system is designed to carry out not only the determination of the calcium concentration by use of fluorescence, but also normal microscopic observation. In FIG. 6, a visible light source 20a emits light for microscopic observation of the sample cell 10. The visible light emitted from the source 20a is condensed by a condenser lens 20b and is radiated on the sample cell 10. The radiated visible light passes through the sample cell 10 and reaches the eyepiece 12 through the optical system for observation. In other words, the visible light travels through a transmission-type light path in the mode of normal microscopic observation. By virtue of this structure, a bright-field image of a cell can be obtained. A Nomarski image can be obtained by combining the fluorescent microscope with a Nomarski condenser IM2-LWDNC (manufactured by Olympus Optical Co., Ltd.), a Nomarski slider IM2-NA (Olympus Optical Co., Ltd.). and a Nomarski objective lens LWDCD Plan 40x (Olympus Optical Co., Ltd.). In addition, a phase contrast image can be obtained by combining the fluorescent microscope with a phase contrast condenser IMT-2-LWCD (Olympus Optical Co., Ltd.) and a phase contrast objective lens LWDCD Plan 40x-PL (Olympus Optical Co., Ltd.). Furthermore, a polarization image can be obtained by combining the fluorescent microscope with a Nomarski condenser IM2-LWDNC (Olympus Optical Co., Ltd.) and a Nomarski objective lens LWDCD Plan 40x (Olympus Optical Co., Ltd.).

Referring to FIG. 7, the fluorescent microscope system will now be described in detail. As is shown in FIG. 7, the filter unit 6 has three interference filters for selectively passing only excitation light having a wavelength of 340 nm, 360 nm or 380 nm. One of the three interference filters is positioned on the optical axis, so that excitation light required for two-wavelength determination using fura-2 can be taken out from the light emitted from the Hg lamp 2. In addition, the filter unit 6 has a plurality of ND filters 4. The ND filters 4 are employed to control the intensities of the excitation lights having different wavelengths, which are used for the determination. Specifically, two lights having different wavelengths, which are used for the two-wavelength determination, must have substantially the same intensity. The light from the Hg lamp 2, however, has different intensities at respective wavelengths. Thus, the intensities of light are adjusted through the ND filters 4. The ND filter 4 and the interference filter 5 can be moved in a direction crossing the light path by means of stepping motors 18, thus enabling desired filters to be positioned on the light path.

Though not shown, a second ND filter is provided for the purpose of correction, which is required when the objective lens 8 is changed. For this purpose, a plurality of ND filters having different transmissivities, e.g. 0%, 25%, 40%, and 100%, are employed, and a desirable one is positioned on the light path.

As is shown in FIG. 7, a dichroic mirror 7 is located on the optical axis of the Hg lamp 2. The dichroic mirror 7 is provided just below the objective lens 8 shown in FIG. 6. The excitation light, which has passed through the filter unit 6, is reflected by the dichroic mirror 7 and is radiated on the sample cell 10 through the objective lens 8. Fluorescence light produced in the sample cell is made incident on the dichroic mirror 7 through the objective lens 8. The dichroic mirror 7 has a function of allowing the fluorescence light to pass through. An emission filter 19 is situated just below the dichroic mirror 7. The emission filter 19 allows only fluorescence light having a wavelength of 510 nm and used for fluorescence determination using fura-2 to pass through. The fluorescence light having the wavelength of 510 nm, which has passed through the emission filter 19, enters a beam splitter (not shown). 20% of the incident light passes through the beam splitter and reaches the eyepiece 12 (shown in FIG. 6) through an optical system (not shown). On the other hand, 80% of the incident light enters the TV camera 13 through another optical system.

The TV camera 13 is connected to the image processor 14. The image processor 14 functions to control the TV camera 13 and to integrate image data sent from the TV camera 13. The image processor 14 is connected to the computer 15, in which a RAM disc is mounted, the monitor 16, and the printer 17 in this order. The computer 15 processes integrated image data sent from the image processor 14, thereby obtaining a calcium concentration and a calcium concentration distribution. The computer 15 is connected to the stepping motors 18 to control the operation of the motors 18.

In the above-described fluorescent microscope, the fluorescence wavelength is fixed and the excitation wavelength is changed. Inversely, the excitation wavelength may be fixed and the fluorescence wavelength may be changed. In this case, it is possible to use a fluorescent probe, such as Indo-1, which has a variable fluorescent spectrum.

When the above-described fluorescent microscope is used and fura-2 is used as the fluorescent probe, a concentration distribution image of calcium ions in a cell can be obtained in the following manner.

Fluorescence light emitted from the sample cell 10 enters the TV camera 13. The TV camera 13 converts the input fluorescence light into electric signals which are proportional to the intensity of the input light and correspond to all individual pixels. The image data in the form of electric signals is input to the image processor 14. The TV camera 13 inputs image data to the image processor 14 at every predetermined exposure time (generally, 1/30 sec). The image processor 14 integrates the input image data a predetermined number of times. An image produced by the integration is input to the computer 15.

The image data from the image processor 14 is written in a frame memory in the computer 15. The image data written in the frame memory is stored in a built-in RAM disc. In the case of two-wavelength determination, a measured image (first image) obtained with a first wavelength and a measured image (second image) obtained with a second wavelength are stored individually. For example, when fura-2 is used in the determination, the first image is obtained with the excitation wavelength of 340 nm, and the second image is obtained with the excitation wavelength of 360 nm.

In accordance with image processing programs, the computer 15 compares the first and second images with respect to all individual pixels, thereby finding the ratio (e.g. I340/I360) of the fluorescence intensities. Then, the ratio of the fluorescence intensities is converted to a calcium concentration on the basis of the calibration curve as shown in FIG. 3. In accordance with the obtained calcium concentration, each pixel is provided with an artificial color. More specifically, pixels having the same calcium concentration are provided with the same artificial color, and pixels having different calcium concentrations are provided with different artificial colors. As a result, calcium concentrations in the respective parts of the cell are represented by colors corresponding to specific concentrations. Moreover, a calcium concentration distribution in the cell can easily be understood by virtue of the use of colors corresponding to specific concentrations.

It should be noted that the image data written in the RAM disc in the computer 15 at each stage can be stored in a floppy disc, if necessary. The image data stored in the RAM disc of the computer 15 or in the floppy disc can be displayed on the screen of the monitor 16, with artificial colors added thereto. As a result, the calcium concentration in the cell can be observed in the form of a color image. When necessary, a hard copy of the color image can be printed out by the printer 17.

As can be seen from the above, according to the above-described fluorescent microscope system, the data obtained by the fluorescent microscope is image-processed, and a two-dimensional calcium concentration distribution in a cell can be observed. However, as has been stated above, according to this technique, a background fluorescence value cannot be determined objectively, and the concentration distribution image cannot be displayed in relation to the cell contour or the cell structure.

A description will now be given of an embodiment in which the problems have been solved by use of the method of the present invention.

Figure 8:
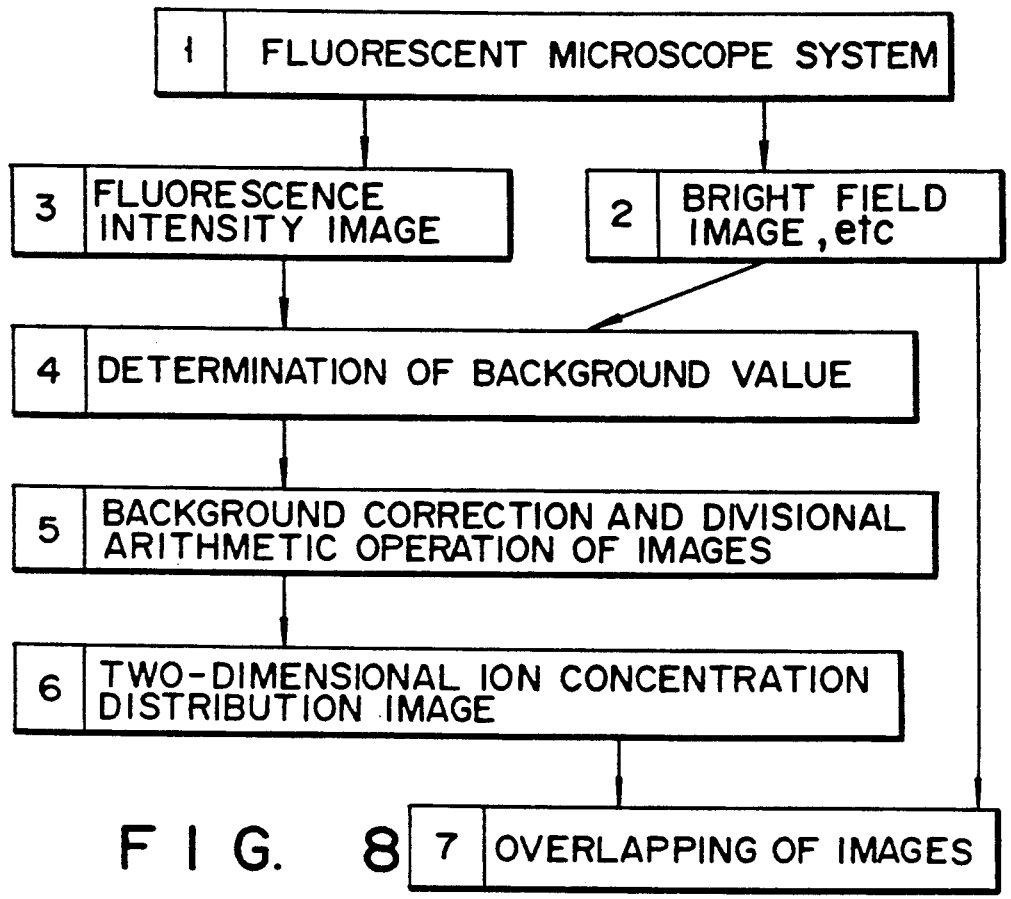
FIG. 8 is a flowchart for illustrating an embodiment of this invention.

This embodiment will be described with reference to a flowchart of FIG. 8. In step 1, the above-described fluorescent microscope system is used, and an established nerve cell line (NG108, N115) is set on the stage 9 as sample cell 10. In subsequent step 2, a bright-field image of the sample cell 10 is obtained. FIG. 9 is a photograph showing the monochromatic bright-field image. As can be seen from FIG. 9, the contour and internal structure of the cell are clearly shown in the bright field image. The image data of the bright-field image is stored in the computer 15.

In step 3, fura-2 is administered, as fluorescent probe, to the sample cell 10. Using two excitation lights having wavelengths of 340 nm and 360 nm, the intensity of fluorescence light having a wavelength of 510 nm is determined, thereby obtaining two fluorescence intensity images. The two fluorescence intensity images are stored in the computer 15.

Figure 10:
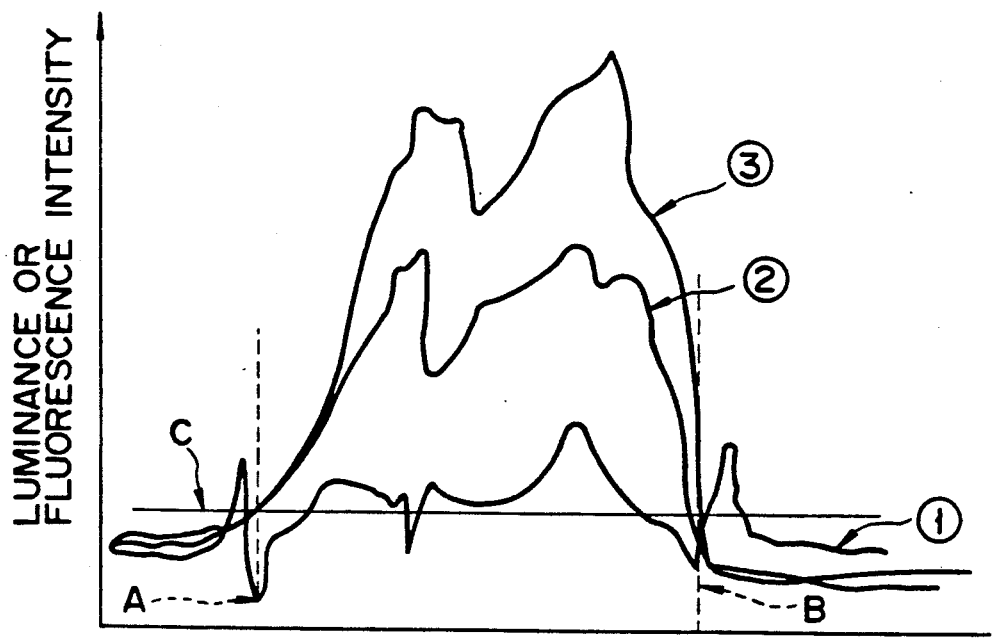
FIG. 10 is a graph for illustrating a method of determining a background fluorescence value according to the embodiment of the invention.

In step 4, a background fluorescence value is determined in the following manner. On the basis of the bright-field image stored in the computer 15, a luminance profile along the X—X line in FIG. 9 is displayed on the monitor 16. Then, on the basis of the two fluorescence intensity images stored in the computer 15, a fluorescence intensity profile is displayed on the monitor 16 at the same position as the luminance profile in an overlapping manner. The overlapped display is possible without performing coordinate transformation. FIG. 10 shows the overlapped displayed profiles. Curve ①is a luminance profile of the bright-field image, curve ② is a fluorescence intensity profile obtained when the excitation wavelength is 340 nm, and curve ③ is a fluorescence intensity profile obtained when the excitation wavelength is 360 nm. From the luminance profile ① of the bright-field image, it is understood that the locations indicated by broken lines A and B correspond to the contour of the cell. The portion of the fluorescence intensity profiles outside the broken lines A and B indicates the background fluorescence light outside the cell. Thus, the background fluorescence value can be determined on the basis of the fluorescence intensity (in this example, 10) at the crossing points between the broken lines A and B and the fluorescence intensity profile curves ② and ③. A straight line C indicates the background level thus determined. By this method, the background fluorescence value can be determined objectively and exactly. If an inexact background value (e.g. 5 or 15) was determined, a two-dimensional calcium concentration distribution image obtained in the subsequent step would not coincide with the cell region of the bright-field image.

In step 5, the two fluorescence intensity images stored in the computer 15 are corrected on the basis of the determined background fluorescence value. This correction is carried out by subtracting the background fluorescence value from the fluorescence intensity value at each point of the fluorescence intensity images. Then, the corrected two fluorescence intensity images are image-processed by the computer 15, and divisional arithmetic operation of images is carried out. Thus, an image having pixels representative of values of I34-0/I360 is obtained.

In step 6, the fluorescence intensity ratio obtained in step 5 is converted to a calcium concentration on the basis of the calibration curve shown in FIG. 3. Further, each pixel of the image is provided with an artificial color in accordance with the obtained calicum concentration, thereby obtaining a two-dimensional concentration distribution image in which pixels corresponding to the same calcium concentration are provided with the same artificial color. FIG. 11 is a photograph showing the obtained two-dimensional concentration distribution image. Though the photograph of FIG. 11 is monochromatic, the actual photograph is a color photograph in which pixels are provided with artificial colors in accordance with calcium concentrations. The two-dimensional concentration distribution image is stored in the computer 15.

In the final step 7, the two-dimensional concentration distribution image is overlapped with the bright-field image obtained in step 2. The overlapping step is carried out by means of affine transformation and exclusive-OR (XOR) operation, as has been explained with reference to FIG. 5. The transformation and operation are performed by the computer 15. FIG. 12 is a photograph showing the obtained overlapped image. Though the photograph of FIG. 12 is monochromatic, the actual photograph is a color photograph in which an artificial color image representing a calcium concentration distribution is shown over the monochromatic bright-field image of the cell. In this composite image, the calcium concentration distribution in the cell is clearly shown in relation to the cell contour or the cell structure.

In the above embodiments, the bright-field image was used as a cell image. However, the cell image may be selected among a bright-field image, a phase contrast image, a Nomarski differential interference contrast image and a polarization image, so that the luminance within the cell may be clearly distinguished from that outside the cell.

The above embodiments relate to the determination of the calcium ion concentration in the cell. However, the present invention is also applicable to the determination of the concentration of hydrogen ions or the concentration of macromolecules such as protein. In either case, the same effects can be attained.

As has been described above, according to the present invention, salient effects can be attained. For example, a two-dimensional concentration distribution in a cell can be produced in relation to the contour of the cell. In addition, the level of background fluorescence light can be set objectively to exactly determine the ion concentration.

Additional advantages and modifications will readily occur to those skilled in the art. Therefore, the invention in its broader aspects is not limited to the specific details, and illustrated examples shown and described herein. Accordingly, various modifications may be made without departing from the spirit or scope of the general inventive concept as defined by the appended claims and their equivalents.

What is claimed is:

1. A method of forming a two-dimensional concentration distribution image of specific ions to be assayed in a living cell, on the basis of the variation in fluorescent spectrum or excitation spectrum of a fluorescent probe, said method comprising the steps of:
   administering a fluorescent probe into a cell;
   obtaining a fluorescence intensity distribution image by determining fluorescence light from the fluorescent probe in a region including the cell;
   measuring the cell optically, thereby obtaining a cell image of the cell selected from the group consisting of a bright-field image, a phase contrast image, a Nomarski differential interference contrast image, and a polarization image;
   determining a background fluorescence value from a profile of the fluorescence intensity image and a profile of the cell image;
   forming a two-dimensional concentration distribution image of the ions to be assayed, by image processing including a subtraction of the background fluorescence value from the fluorescence intensity distribution image; and
   subjecting the cell image and the two-dimensional concentration distribution image of the ions to image processing, thereby displaying both images in an overlapping manner.

2. The method according to claim 1, wherein said step of obtaining a cell image is carried out prior to the step of obtaining a fluorescence intensity distribution image by determining fluorescence light.

3. The method according to claim 1, wherein a two-dimensional concentration distribution image of calcium ions in a living cell is formed by use of the fluorescent probe selected from the group consisting of fura-2, Quin-2, and Indo-1.

4. The method according to claim 1, wherein image data of the two-dimensional ion concentration distribution image is subjected to affine transformation, in order to make the coordinate system of the two-dimensional ion concentration distribution image coincide with the coordinate system of the data of the cell image.

5. The method according to claim 1, wherein said cell image is a monochromatic image, and said two-dimensional ion concentration distribution image is a multi-color image having colors corresponding to ion concentrations.

6. The method according to claim 1, wherein the overlapped display of the cell image and the two-dimensional ion concentration distribution image is performed by means of an exclusive-OR operation.

* * * * *